United States Patent

Maurer et al.

[11] 3,981,993
[45] Sept. 21, 1976

[54] O-ALKYL-O-N-PROPYL-O-PYRIMIDIN(2)YL-THIONO-PHOSPHORIC ACID ESTERS

[75] Inventors: Fritz Maurer, Wuppertal; Ingeborg Hammann, Cologne; Bernhard Homeyer, Opladen, all of Germany

[73] Assignee: Bayer Aktiengesellschaft, Leverkusen, Germany

[22] Filed: Mar. 12, 1975

[21] Appl. No.: 557,699

[30] Foreign Application Priority Data
Mar. 28, 1974 Germany............................ 2415058

[52] U.S. Cl. ............................ 424/200; 260/251 P
[51] Int. Cl.² ...................... C07F 9/65; A01N 9/36
[58] Field of Search .................. 260/251 P; 424/200

[56] References Cited
UNITED STATES PATENTS
3,607,991  9/1971  Peterson et al. ..................... 260/973
3,741,968  6/1973  Haubein .......................... 260/251 P FOREIGN PATENTS OR APPLICATIONS
546,259  2/1974  Switzerland
300,740  8/1954  Switzerland

*Primary Examiner*—Nicholas S. Rizzo
*Assistant Examiner*—Diana G. Rivers
*Attorney, Agent, or Firm*—Burgess, Dinklage & Sprung

[57] ABSTRACT

O-alkyl-O-n-propyl-O-pyrimidin(2)yl-thiono-phosphoric acid esters of the formula

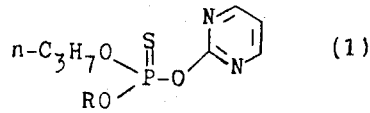

in which
R is methyl or ethyl, which possess insecticidal, acaricidal and nematocidal properties.

9 Claims, No Drawings

O-ALKYL-O-N-PROPYL-O-PYRIMIDIN(2)YL-THIONO-PHOSPHORIC ACID ESTERS

The present invention relates to and has for its objects the provision of O-methyl- and O-ethyl-O-n-propyl-O-yrimidin(22)yl-thionophosphoric acid esters, which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from U.S. Pat. No. 2,754,243 that O,O-diethyl-O-[2-isopropyl-4-methyl-pyrimidin(6)yl]-thionophosphoric acid ester (Compound A) exhibits insecticidal and acaricidal properties.

The present invention )yl-thionophosphoric pyrimidin(2)yl-thiono-phosphoric acid esters of the general formula

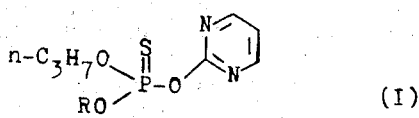

(I)

in which

R is methyl or ethyl.

Surprisingly, the pyrimidin(2)yl-thionophosphoric acid esters (I) according to the invention are distinguished by a better insecticidal, including soil-insecticidal, acaricidal and nematocidal action than the previously known O,O-diethyl-O-[2-isopropyl-4-methyl-pyrimidin(6)yl]-thionophosphoric acid ester of analogous structure and of the same type of action. Accordingly, the compounds according to the invention represent a genuine enrichment of the art.

The invention also provides a process for the production of a pyrimidin(2)yl-thionophosphoric acid ester of the formula (I) in which an O,O-dialkylthionophosphoric acid diester halide of the general formula

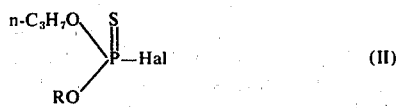

(II)

in which

R has the abovementioned meaning and

Hal is halogen, preferably chlorine, is reacted either with the hydrochloride of 2-hydroxypyrimidine optionally in the presence of an acid acceptor, or with an alkali metal salt, alkaline earth metal salt or ammonium salt of 2-hydroxypyrimidine.

2-hydroxypyrimidine has the formula

(III)

If, for example, O-n-propyl-O-ethyl-thionophosphoric acid diester chloride and the hydrochloride of 2-hydroxypyrimidine are used as starting materials, the course of the reaction can be represented by the following formula scheme:

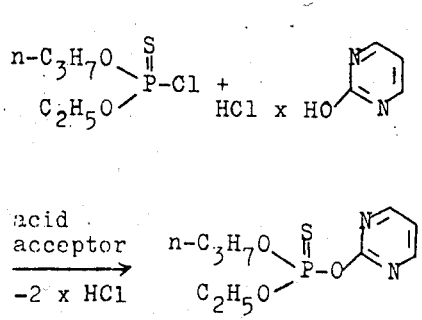

The formulae (II) and (III) provide a general unambiguous definition of the O,O-dialkylthionophosphoric acid diester halides which can be used as starting materials, and of 2-hydroxypyrimidine. The O,O-dialkylthionophosphoric acid diester halides (II) are described in the literature and obtainable according to customary processes, as is the hydrochloride of 2-hydroxypyrimidine (III), which may be prepared from 1,1,3,3-tetramethoxypropane and urea in alcoholic solution by the action of hydrogen chloride according to U.S. Pat. No. 3,741,968.

The reaction according to the invention is preferably carried out in the presence of a solvent which term includes a mere diluent. Practically all inert organic solvents can be used for this purpose. These include, in particular, aliphatic and aromatic, optionally chlorinated, hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate, methylate and ethylate and potassium carbonate, methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 10° to 100°, preferably at 35° to 60°C.

The reaction is in general allowed to take place under normal pressure.

In carrying out the process, the starting materials are generally employed in equimolar ratios. An excess of one or the other reactant in general produces no significant advantages. The reaction is preferably carried out in the presence of one of the abovementioned solvents, if appropriate in the presence of an acid acceptor, at the temperatures indicated. After a reaction time of from one to several hours, in most cases at an elevated temperature, the batch is cooled and the reaction mixture is poured into water and taken up in an organic solvent, for example toluene. The reaction mixture is then worked up in the usual manner by drying the organic phase and evaporating the solvent.

The new compounds are obtained in the form of oils which cannot be distilled without decomposition but can be freed from the last volatile constituents by so-called "slight distillation", that is to say prolonged heating under reduced pressure to moderately elevated temperatures, and can be purified in this way. They are characterized by their refractive indexes.

As has already been mentioned, the pyrimidin(2)yl-thionophosphoric acid esters according to the invention are distinguished by an excellent insecticidal, including soil-insecticidal, acaricidal and nematocidal activity. They are active against plant pests, hygiene pests and pests of stored products and couple a low phytotoxicity with a good action against both sucking and biting insects and mites.

For this reason, the compounds according to the invention can be employed successfully as pesticides in plant protection and also in the hygiene field and the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hesderae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cottom worm (Prodenia litura), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*, the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus* = *panonychus ulmi*), gall mites, for example the blackcurrant gall mite (*Eriophyes ribis*) and tersonemides, for example the broad mite (*Hemitarsonemus latus*) and the cyclamen mite (*Tarsonemus pallidus*); finally, ticks, such as the relapsing fever tick (*Ornithodorus moubata*).

The active compounds according to the invention combine a low toxicity to warm-blooded animals with strong nematocidal properties and can therefore be used to combat nematodes, especially phytopathogenic nematodes. These essentially include leaf nematodes (Arphelenchoides), such as the chrysanthemum eelworm (*A. ritzemabosi*), the leaf-blotch eelworm (*A. fragariae*), and the rice eelworm (*A. oryzae*); stem nematodes (Ditylenchus), such as the stem eelworm (*D. dipsaci*); root-knot nematodes (Meloidogyne), such as *M. areharia* and *M. incognita*; cyst-forming nematodes (Heterodera), such as the potato cyst eelworm (H. rostochiensis), and the beet cyst eelworm (*H. schachtii*); and also root nematodes which live free, for example of the genera Pratylenchus, Paratylenchus, Rotylenchus, Xiphinema and Radopholus.

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usuable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, and nematocides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001-10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Laphygma test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew moist and were then infested with caterpillars of the owlet moth (*Laphygma exigua*).

After the specified periods of time, the degree of destruction in % was determined. 100% means that all caterpillars had been killed while 0% indicates that no caterpillars had been killed.

The active compounds, the concentrations of the active compounds, the evaluation times and the results can be seen from Table 1:

Table 1

(*Laphygma* test)

| Active Compound | Active Compound concentration in % by weight | Degree of destruction in % after 3 days |
|---|---|---|
| 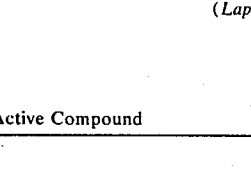<br>(A) (known) | 0.004 | 100 |
| 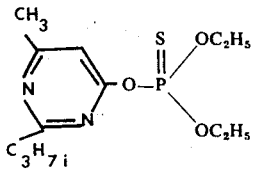<br>(2) | 0.004<br>0.0008 | 100<br>100 |
| 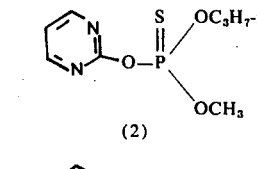<br>(1) | 0.004<br>0.0008 | 100<br>65 |

EXAMPLE 2

Doralis test (systemic action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Vicia faba*) which had been heavily infested with the bean aphid (*Doralis fabae*) were watered with the preparation of the active compound so that the preparation penetrated into the soil without wetting the leaves of the bean plants. The active compound was taken up by the bean plants from the soil and thus passed to be infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from Table 2:

Table 2

(*Doralis* test/systemic action)

| Active compound | Active compound concentration in % by weight | Degree of destruction in % after 4 days |
|---|---|---|
| 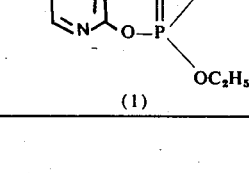<br>(A) (known) | 0.1<br>0.02 | 50<br>0 |
| 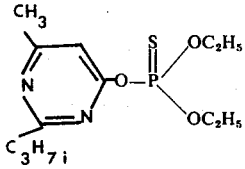 | 0.02 | 100 |
| 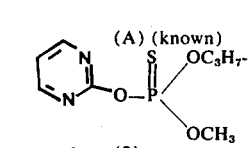<br>(1) | 0.02 | 100 |

EXAMPLE 3

Phaedon larvae test (long-term action after watering)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage plants (*Brassica oleracea*) were each watered with 50 ml of the preparation of the active compound so that the preparation penetrated into the soil without wetting the leaves of the cabbage plants. The active compound was taken up by the cabbage plants from the soil and thus passed to the leaves.

After the indicated times, the plants were infested with mustard beetle larvae (*Phaedon cochleariae*) and their destruction was determined at intervals of 3 days. 100% means that all beetle larvae had been killed and 0% means that none of the beetle larvae had been killed.

The active compounds, the concentrations of the active compounds, the evaluation times and the results can be seen from Table 3:

Table 3

Long-term action after watering/0.025% of active compound
(*Phaedon* larvae on *Brassica oleracea*)

| Active Compound | % destruction after days | | | | |
|---|---|---|---|---|---|
| | 4 | 8 | 11 | 15 | 18 |
| 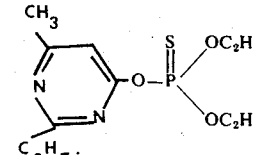<br>(A) (Known) | 100 | 50 | | | |

Table 3-continued

Long-term action after watering/0.025%
of active compound
(Phaedon larvae on Brassica oleracea)

| Active Compound | % destruction after days | | | | |
|---|---|---|---|---|---|
| | 4 | 8 | 11 | 15 | 18 |
| 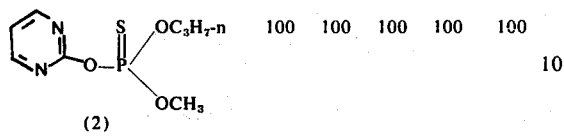 (2) | 100 | 100 | 100 | 100 | 100 |
| 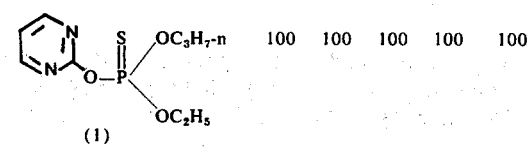 (1) | 100 | 100 | 100 | 100 | 100 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (Phaseolus vulgaris), which had a height of approximately 10–30 cm, were sprayed with the preparation of the active compound until dripping wet. These bean plants were heavily infested with the common or two-spotted spider mite (Tetranychus urticae) in all stages of development.

After the specified periods of time, the effectiveness of the preparation of active compound was determined by counting the dead mites. The degree of destruction thus obtained is expressed as a percentage: 100% means that all the spider mites were killed whereas 0% means that none of the spider mites were killed.

The active compounds, the concentrations of the active compounds, the evaluation times and the results can be seen from Table 4:

Table 4

| Active Compound | (Tetranychus test/resistant) Active compound concentration in % by weight | Degree of destruction in % after 2 days |
|---|---|---|
| 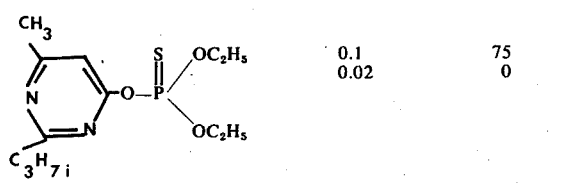 (A) (known) | 0.1 | 75 |
| | 0.02 | 0 |
| 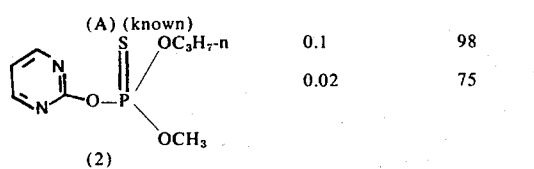 (2) | 0.1 | 98 |
| | 0.02 | 75 |

Table 4-continued

| Active Compound | (Tetranychus test/resistant) Active compound concentration in % by weight | Degree of destruction in % after 2 days |
|---|---|---|
| 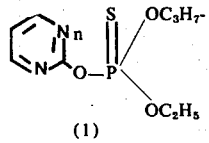 (1) | 0.1 | 98 |
| | 0.02 | 45 |

EXAMPLE 5

Critical concentration test
Test nematode: Meloidogyne sp.
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which was given in p.p.m., was decisive. The soil was filled into pots, lettuce was sown in and the pots were kept at a greenhouse temperature of 27°C. After 4 weeks, the lettuce roots were examined for infestation with nematodes, and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from Table 5:

Table 5

| Active Compound | (Critical concentration test/Meloidogyne sp) Degree of destruction in % at an active compound concentration of | | | | |
|---|---|---|---|---|---|
| | 20 | 10 | 5 | 2.5 | 1.25 ppm |
| 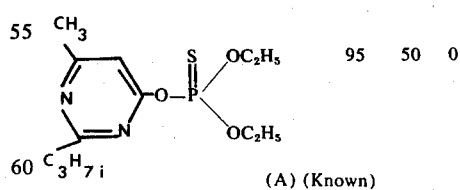 (A) (Known) | 95 | 50 | 0 | | |
| 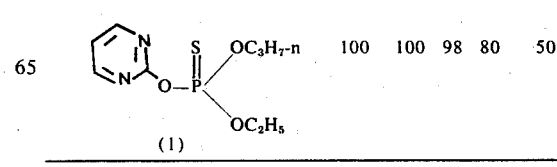 (1) | 100 | 100 | 98 | 80 | 50 |

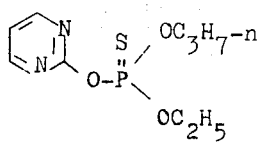

(1)

20.2 g (0.1 mole) of O-ethyl-O-n-propyl-thionophosphoric acid diester chloride were added to a mixture of 13.2 g (0.1 mole) of 2-hydroxy-pyrimidine hydrochloride. 34.5 g (0.25 mole) of potassium carbonate and 200 ml of acetonitrile at 40° to 50°C. The batch was stirred for a further 3 hours at 40°–50°C and then poured into 600 ml of water, and the reaction product was extracted by shaking twice with toluene. The organic phases were washed with saturated sodium bicarbonate solution, dried over sodium sulfate and freed from the solvent under reduced pressure. 19.4 g (74% of theory) of O-ethyl-O-n-propyl-O-[pyrimidin(2)yl]-thionophosphoric acid ester remained in the form of a yellow oil of refractive index $n_D^{23}$: 1.5140.

EXAMPLE 7

O-Methyl-O-n-propyl-O-[pyrimidin(2)yl]-thionophosphoric acid ester of the formula

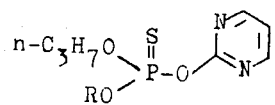

(2)

was prepared analogously to the description in Example 6, in a yield of 71% of theory, and with a refractive index of $n_D^{23}$: 1.5137.

It will be appreciated that the instant specification and examples are set forth by way of illustration and not limitation, and that various modifications and changes may be made without departing from the spirit and scope of the present invention.

What is claimed is:

1. An O-alkyl-O-n-propyl-O-pyrimidin(2)yl-thionophosphoric acid ester of the formula

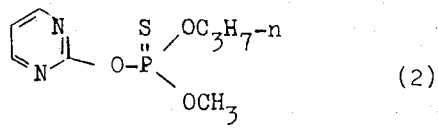

in which R is methyl or ethyl.

2. A compound according to claim 1 in which said compound is O-ethyl-O-n-propyl-O-[pyrimidin(2)yl]-thionophosphoric acid ester of the formula

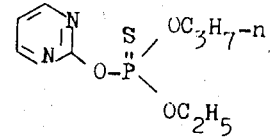

3. A compound according to claim 1 in which said compound is O-methyl-O-n-propyl-O-[pyrimidin(2)yl]-thionophosphoric acid ester of the formula 4. An insecticidal, acaricidal or nematocidal composition containing as active ingredient an insecticidally, acaricidally or nematodically effective amount of a compound according to claim 1 in admixture with a diluent.

5. A composition according to claim 4 wherein said compound is O-ethyl-O-n-propyl-O-[pyrimidin(2)yl]-thionophosphoric acid ester.

6. A composition according to claim 4 wherein said compound is O-methyl-O-n-propyl-O-[pyrimidin(-2)yl]-thionophosphoric acid ester.

7. A method of combating insect, acarid or nematode pests which comprises applying to the pests or a habitat thereof an insecticidally, acaricidally or nematocidally effective amount of a compound according to claim 1.

8. The method according to claim 7 wherein said compound is O-ethyl-O-n-propyl-O-[pyrimidin(2)yl]-thionophsophoric acid ester.

9. The method according to claim 7 wherein said compound is O-methyl-O-n-propyl-O-[pyrimidin(-2)yl]-thionophosphoric acid ester.

* * * * *